United States Patent [19]

Auerbach

[11] Patent Number: 5,044,492

[45] Date of Patent: Sep. 3, 1991

[54] ORIENTATION-INDICATING CONDOM PACKAGE

[76] Inventor: Abraham E. Auerbach, P.O. Box 256, Oracle, Ariz. 85623

[21] Appl. No.: 569,634

[22] Filed: Aug. 20, 1990

[51] Int. Cl.$^5$ ........................................... B65D 85/00
[52] U.S. Cl. ...................................... 206/69; 206/459
[58] Field of Search .................... 206/37, 69, 459, 484

[56] References Cited

U.S. PATENT DOCUMENTS

| | | | |
|---|---|---|---|
| 2,008,875 | 7/1935 | Peterson et al. | 206/69 |
| 2,365,556 | 12/1944 | Karg | 206/69 |
| 3,136,417 | 6/1964 | Clinch | 206/69 |
| 4,741,434 | 5/1988 | Liebman | 206/69 |
| 4,869,723 | 9/1989 | Harmon | 206/69 |
| 4,874,096 | 10/1989 | Tessera-Chiesa | 206/459 |
| 4,875,491 | 10/1989 | Parrone | 206/69 |
| 4,890,739 | 1/1990 | Mize, Jr. et al. | 206/484 |
| 4,895,257 | 1/1990 | Winslow | 206/459 |
| 4,925,033 | 5/1990 | Stoner | 206/69 |

FOREIGN PATENT DOCUMENTS 0499098  1/1939  United Kingdom ................. 206/69

Primary Examiner—Jimmy G. Foster

[57] ABSTRACT

A package for an individual condom contains a rolled condom and bears an exterior tactile indication of the orientation of the condom within. The indication is one or more protrusions formed in the material of the package or a piece of suitable material adhesively applied. This indication enables a user to readily determine the "top" and "bottom" of the rolled condom within, even in darkness. Hence the condom may be removed from the package and placed with correct orientation onto a penis without the delay, frustration, and needless handling (with possible soiling) that can result from an incorrect orientation.

6 Claims, 1 Drawing Sheet

ORIENTATION-INDICATING CONDOM PACKAGE

BACKGROUND

1. Field of Invention

This invention relates to condom packages, particularly to an individual condom package which provides a user-aiding function.

2. Discussion of Prior Art

Condoms are generally supplied in individual packages of waterproof paper, plastic, foil, etc., which the user can conveniently tear open to access the condom inside. The condom customarily is rolled so that it has a circular central flat web surrounded by a rolled, integral, relatively thick edge that extends up from a top surface of the web. To apply it on the penis, one must place it with the bottom side of the web against the tip of the penis and then unroll it down onto the penis. Condoms usually are applied in darkness or dim light, where one cannot see the orientation of the condom. And the soft material of the condom makes it difficult to determine the orientation by feel. Also, condoms are frequently handled in haste.

All this can lead to serious problems. If the condom happens to be placed with the top surface of the web against the tip of the penis, i.e., "upside down" on the penis, it cannot be unrolled and frustration, exasperation, and delay may result until the user discovers what has happened. Such emotions and delay are undesirable at any time, but especially at such times as condoms are used. Further, such delay can defeat the contraceptive purpose of the condom, for seminal fluid may be deposited on the very surface of the condom that is exposed when the condom is finally applied correctly! It is known that condoms sometimes fail to prevent conception and this may well be one reason. Further, any needless handling of a condom increases the risk of soiling it, so that it may become a carrier of infection.

OBJECTS

It is accordingly one object of this invention to provide a means by which the user can quickly and positively determine the orientation of a condom in dim light or darkness, before opening the individual condom package, so that delay is avoided and the user need not rely on feeling the condom itself.

Other objects are to provide a way to apply a condom to a penis rapidly, with proper orientation, without trial-and-error and potential frustration, and with little or no additional cost.

Further objects and advantages will become apparent from a consultation of the accompanying drawings and ensuing description.

DRAWINGS

DESCRIPTION

Figure 1:
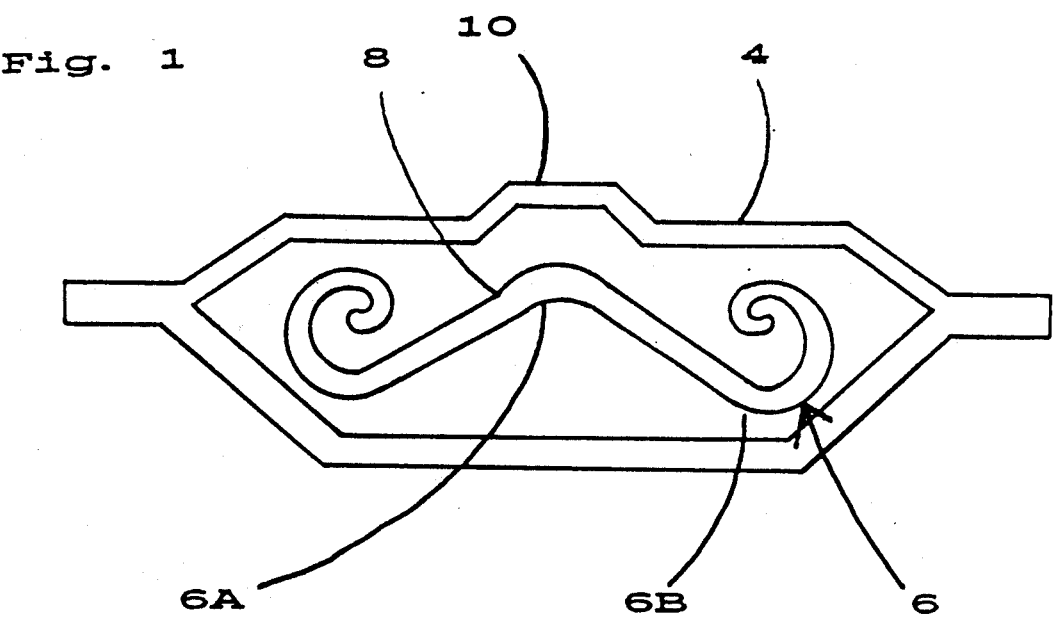
FIG. 1 is a cross-sectional side view of an individual condom package according to the invention.
Figure 2:
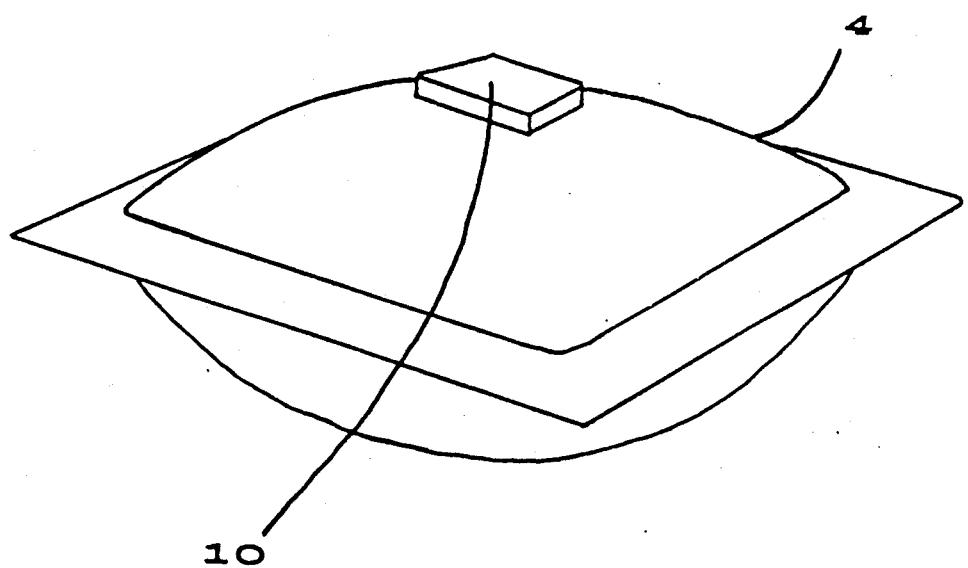
FIG. 2 is a plan view of the package of FIG. 1.

FIGS. 1-2—Package With Integral Nub

Referring to FIG. 1, condom package 4 is totally sealed and contains condom 6, rolled as shown, with a semen reservoir or tip 8 which faces upward. Condom 6 comprises a circular central portion 6A and an annular rolled thick edge portion 6B, oriented around central portion 6A and adjacent the outer portions of the inside of package 4. A protrusion, boss or nubbin (hub) 10 is formed integral with the top side and on the outside of package 4. Nub 10 indicates the top of condom 6. Package 4 is composed of any suitable material in which protrusion 10 can be formed. For example, foil, plastic, paper, etc. can have protrusion 10 embossed thereon.

As shown in the perspective view of FIG. 2, protrusion 10 is made square, for extra tactile perceptibility. A typical package may be 55 mm square and 5 mm thick, with protrusion 10 being about 1 mm high by 9 mm wide on each side.

Figure 3:
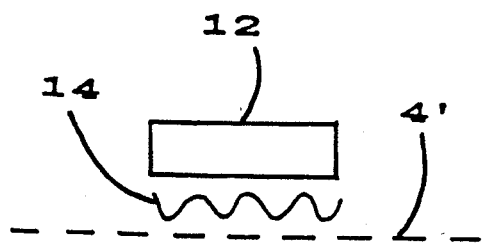
FIG. 3 is a cross-section of an adhesively applied member according to the invention.

FIG. 3—Package With Separate Nub

Note from FIGS. 1 and 2 that the package or container 4 has two major sides (upper and lower). Each side has an external surface and an internal surface. The external surfaces face in opposing directions and the internal surfaces face each other. The internal surfaces have portions which are spaced apart in a first direction generally normal to the major sides so as to define the volume within the package. The volume has a first or thickness dimension measured vertically or in the first direction between the corresponding spaced-apart portions of the sides. The volume has a second or width dimension measured horizontally or in a second direction generally parallel to the sides and perpendicular to the first direction. The width is the minimum size of the volume in the second direction and is larger than the thickness of the volume. Nub 10 on the external surface of the upper side is a tactile means for indicating the orientation of condom 6 within the container. The area of the nub, as measured parallel to the upper side, is smaller than the area of either spaced-apart portion.

According to another embodiment, nub or protrusion 12 may be separate from the package. In this case a nubless package 4' has a separate nub 12, e.g., of rubber, and about the same size as nup 10, applied by means of adhesive 14 to one side of package 4'.

Note from FIG. 3 that nub 12 on the external surface of the upper side is also a tactile, adhesively secured means for indicating the orientation of condom 6 within the container. Again, the area of the nub, as measured parallel to the upper side, is smaller than the area of either spaced-apart portion.

OPERATION

To use the condom, the user first grips package 4 (or 4' of FIG. 3) and notes the upper or top side by feeling for nub 10 or 12. Then he or she turns the package (if necessary) so that it is oriented correctly, i.e., with its top side (nub 10 or 12) up. Then, while preserving the correct orientation, the user opens the package in the conventional manner, e.g., by ripping off an edge strip. The user then removes condom 6 from the package while still maintaining its orientation, i.e., top side up as shown in FIG. 1. Then, without changing its orientation, the user places the condom on the penis by placing its bottom side on the tip of the penis and unrolling the condom down onto the penis in conventional fashion. The condom will unroll properly since its bottom side will be against the penis due to its correct orientation.

SUMMARY, RAMIFICATIONS, SCOPE

Thus the reader will see that the distinctive tactile indication provided by the nub on the appropriate side of the condom package avoids potential erroneous orientation of the condom due to haste, dim light, or darkness. This avoids possible delay and frustration which may defeat the contraceptive purpose of the condom. It also avoids excessive handling which can result in damage to or soiling of the condom. Such damage can also defeat the contraceptive purpose of the condom, and soiling may even make it a carrier of infection.

While the above description contains many specificities, these should not be construed as limitations on the scope of the invention, but rather as an exemplification of a preferred embodiment thereof. Many variations are possible within the scope of the invention. For example, the protrusion may be formed with a distinctive design, or simply the words "This Side Up", or a representation of the sun, moon, or stars to convey the idea of something above. This will enable the user, when not in total darkness, to visibly determine the correct orientation. As another example, the tactile protrusion need not be formed in the material of the condom package, but may be applied as a separate, adhesively attached element. Alternatively a protrusion may be applied to the bottom side of the package. The shape and height of the protrusion can vary; circular, rectangular, cruciform, and star shapes are possible. More than one protrusion may be used. The entire surface of one side of the package may be made rough or dotted. The package may be a box of cardboard or plastic, and may have an oval shape. Accordingly, the full scope of the invention should be determined not by the examples given, but by the appended claims and their legal equivalents.

I claim:

1. A condom package, comprising:
a container having a configuration with two major sides, said sides each having an external surface and an internal surface, said external surfaces of said major sides facing in opposing directions, said internal surfaces facing each other, said internal surfaces having corresponding portions which are spaced apart in a first direction normal to said major sides so as to define a volume therebetween,
said volume having a first dimension, designated a thickness, which is measured in said first direction and between said corresponding portions,
said volume having a second dimension, designated a width, which is measured in a second direction generally parallel to said sides and perpendicular to said first direction, said width being the minimum size of said volume in said second direction,
said thickness of said volume being being smaller than said width thereof such that said volume is generally flat,
a rolled condom being enclosed within said volume of said container,
said external surface of one of said major sides of said container containing tactile means for indicating the orientation of said rolled condom within said container, said tactile means comprising an integral protrusion on said corresponding portion of said one major side, said protrusion having an area, as measured parallel to said major sides, which is smaller than the area of said corresponding portion of said one major side.

2. The condom package of claim 1 wherein said container is made of a waterproof and airtight material which can be ruptured by hand.

3. The condom package of claim 1 wherein said major sides of container have a rectangular configuration so that said container has a rectangular configuration when seen from said first direction.

4. A condom package, comprising:
a container having a configuration with two major sides, said sides each having an external surface and an internal surface, said external surfaces of said major sides facing in opposing directions, said internal surfaces facing each other, said internal surfaces having corresponding portions which are spaced apart in a first direction normal to said major sides so as to define a volume therebetween,
said volume having a first dimension, designated a thickness, which is measured in said first direction and between said corresponding portions,
said volume having a second dimension, designated a width, which is measured in a second direction generally parallel to said sides and perpendicular to said first direction, said width being the minimum size of said volume in said second direction,
said thickness of said volume being being smaller than said width thereof such that said volume is generally flat,
a rolled condom being enclosed within said volume of said container,
said external surface of one of said major sides of said container containing tactile means for indicating the orientation of said rolled condom within said container, said tactile means comprising a tactile discernable element which is adhesively secured to said corresponding portion of said one major side, said tactile discernable element having an area, as measured parallel to said one major side, which is smaller than the area of said corresponding portion of said one major side.

5. The condom package of claim 4 wherein said container is made of a waterproof and airtight material which can be ruptured by hand.

6. The condom package of claim 4 wherein said major sides of container have a rectangular configuration so that said container has a rectangular configuration when seen from said first direction.

* * * * *